(12) United States Patent
Krause et al.

(10) Patent No.: US 11,198,942 B2
(45) Date of Patent: Dec. 14, 2021

(54) ELECTROLYSIS SYSTEM FOR CARBON DIOXIDE

(71) Applicant: Siemens Aktiengesellschaft, Munich (DE)

(72) Inventors: Ralf Krause, Herzogenaurach (DE); Christian Reller, Minden (DE); Guenter Schmid, Hemhofen (DE); Elena Volkova, Erlangen (DE)

(73) Assignee: SIEMENS ENERGY GLOBAL GMBH & CO. KG, Munich (DE)

( * ) Notice: Subject to any disclaimer, the term of this patent is extended or adjusted under 35 U.S.C. 154(b) by 302 days.

(21) Appl. No.: 15/548,618

(22) PCT Filed: Dec. 23, 2015

(86) PCT No.: PCT/EP2015/081145
§ 371 (c)(1),
(2) Date: Aug. 3, 2017

(87) PCT Pub. No.: WO2016/124300
PCT Pub. Date: Aug. 11, 2016

(65) Prior Publication Data
US 2018/0023202 A1 Jan. 25, 2018

(30) Foreign Application Priority Data
Feb. 6, 2015 (DE) .................. 10 2015 202 117.3

(51) Int. Cl.
*C25B 3/25* (2021.01)
*C25B 15/08* (2006.01)
(Continued)

(52) U.S. Cl.
CPC .............. *C25B 3/25* (2021.01); *B01J 29/106* (2013.01); *C01B 32/50* (2017.08); *C07C 47/04* (2013.01);
(Continued)

(58) Field of Classification Search
None
See application file for complete search history.

(56) References Cited

U.S. PATENT DOCUMENTS 4,160,816 A * 7/1979 Williams ............... B01J 19/127
136/291
4,223,001 A * 9/1980 Novotny .................. C01B 3/16
252/373
(Continued)

FOREIGN PATENT DOCUMENTS

AU 6811981 A 9/1981 ............. C07C 51/00
CN 102181876 A 9/2011 ............... C25B 1/00
(Continued)

OTHER PUBLICATIONS

Gan et al., "Hydrogen Storage and Delivery: Immobilization of Highly Active Homogeneous Catalyst for Decomposition of Formic Acid to Hydrogen and Carbon Dioxide," React Kinet Catal Lett (2009), vol. 98, pp. 205-213. (Year: 2009).*
(Continued)

*Primary Examiner* — Harry D Wilkins, III
(74) *Attorney, Agent, or Firm* — Slayden Grubert Beard PLLC

(57) ABSTRACT

The present disclosure relates to electrolysis systems and methods. The teachings thereof may be embodied in methods and systems for the utilization of carbon dioxide and production of carbon monoxide. For example, a method may include: passing an electrolyte and carbon dioxide in front of a cathode through a cathode chamber; and removing electrolysis byproducts from an electrolyte/electrolysis product mixture using a catalytic filter system. The cathode may include material to reduce carbon dioxide. The process may generate a hydrocarbon compound or carbon monoxide as the electrolysis product and a formate as an electrolysis byproduct. The filter system may include a functionalized
(Continued)

complex or a functionalized support material which catalyzes a cleavage reaction of formates (a) to hydrogen and carbon dioxide, or (b) to water and carbon monoxide.

7 Claims, 5 Drawing Sheets

(51) Int. Cl.
    *C25B 1/00*     (2021.01)
    *C01B 32/50*     (2017.01)
    *B01J 29/10*     (2006.01)
    *C07C 47/04*     (2006.01)
    *C07C 1/207*     (2006.01)

(52) U.S. Cl.
    CPC ............... *C25B 1/00* (2013.01); *C25B 15/08* (2013.01); *C07C 1/2078* (2013.01)

(56) References Cited

U.S. PATENT DOCUMENTS

| | | | | |
|---|---|---|---|---|
| 7,939,461 | B2* | 5/2011 | Fukuzumi | C01B 3/22 502/230 |
| 2006/0172178 | A1* | 8/2006 | Hashizume | H01M 4/881 429/483 |
| 2010/0034733 | A1* | 2/2010 | Fukuzumi | B01J 31/2295 423/658.2 |
| 2010/0203427 | A1* | 8/2010 | Hasebe | H01M 8/0625 429/524 |
| 2010/0233587 | A1* | 9/2010 | Sato | H01M 4/8657 429/523 |
| 2011/0114504 | A1* | 5/2011 | Sivasankar | C25B 1/02 205/455 |
| 2012/0055804 | A1* | 3/2012 | Bettelheim | C25B 3/04 205/555 |
| 2012/0164554 | A1* | 6/2012 | Suzuki | H01M 4/8657 429/482 |
| 2012/0228147 | A1* | 9/2012 | Sivasankar | C25B 1/003 205/440 |
| 2012/0264027 | A1* | 10/2012 | Mizukami | H01M 4/92 429/427 |

FOREIGN PATENT DOCUMENTS

| | | | | |
|---|---|---|---|---|
| CN | 102190573 | A | 9/2011 | ............ C07C 51/00 |
| DE | 2851225 | A1 | 6/1979 | ............ B01J 19/12 |
| EP | 2832421 | A1 | 2/2015 | ............ B01D 53/22 |
| JP | 07-033421 | A * | 2/1995 | ............ C01B 31/18 |
| WO | 2016/124300 | A1 | 8/2016 | ............ C25B 1/00 |

OTHER PUBLICATIONS

Loges et al., "Catalytic Generation of Hydrogen from Formic Acid and its Derivatives: Useful Hydrogen Storage Materials,," Top Catal (2010), vol. 53, pp. 902-914. (Year: 2010).*
Augustynski et al., Electrochemical reduction of CO2 at metallic electrodes, chapter from Advances in Chemical Conversions for Mitigating Carbon Dioxide, Studies in Surface Science and Catalysis, vol. 114, 1998 (no month), pp. 107-116 (Year: 1998).*
Kortlever et al, Catalysts and Reaction Pathways for the Electrochemical Reduction of Carbon Dioxide, The Journal of Physical Chemistry Letters, vol. 6, No. 20, Sep. 2015, pp. 4073-4082 (Year: 2015).*
Loges et al, Catalytic Generation of Hydrogen from Formic acid and its Derivatives: Useful Hydrogen Storage Materials, Topics in Catalysis, vol. 53, No. 13-14, Aug. 2010, pp. 902-914 (Year: 2010).*
"Hassium", http://en.wikipedia.org/wiki/Hassium, accessed on Jun. 4, 2020 (Year: 2020).*
Inglis et al, Decomposition of formic acid on titanium, vanadium, chromium, manganese, iron, cobalt, nickel, and copper, Journal of the Chemical Society A, 1969 (no month), pp. 2985-2987 (Year: 1969).*
Fellay et al., A Viable Hydrogen-Storage System Based on Selective Formic Acid Decomposition with a Ruthenium Catalyst, Angewandte Chemie, vol. 47, No. 21, May 2008, pp. 3966-3968 (Year: 2008).*
Gan et al, Hydrogen storage and delivery: immobilization of a highly active homogeneous catalyst for the decomposition of formic acid to hydrogen and carbon dioxide, Reaction Kinetics and Catalysis Letters, vol. 98, No. 2, Nov. 2009, pp. 205-213. (Year: 2009).*
Reinäcker, Von G. et al., "Der Thermische Zerfall von Magnesiumformiat, Nickelformiat und Magnesium-Nickelformiat-Mischkristallen Sowie von Gemengen aus Magnesiumformiat mit Nickelformiat, Kobaltformiat und Kupferformiat," Zeitschrift für anorganische und allgemeine Chemie, vol. 307, pp. 235-254 (German language w/ English abstract), Mar. 1, 1960.
DeWulf, David W. et al., "Electrochemical and Surface Studies of Carbon Dioxide Reduction to Methane and Ethylene at Copper Electrodes in Aqueous Solutions," Journal of Electrochemistry Society, vol. 136, No. 6, pp. 1686-1691, 1989.
Tavares, M.T. et al., "Coking and Decoking During Methanation and Methane Decomposition on Ni—Cu Supported Catalysts," Materials and Corrosion, vol. 50, pp. 681-685, Aug. 5, 1999.
Chung, Seung-Young et al., "Electrocatalytic Oxidation of HCOOH on Pt-Based Anodes," Journal of Ind. Eng. Chem., Vo. 13, No. 3, pp. 339-344, Dec. 24, 2006.
Fellay, Céline et al., "A Viable Hydrogen-Storage System Based on Selective Formic Acid Decomposition with a Ruthenium Catalyst," Angewandte Chemie, vol. 120, pp. 4030-4032, 2008.
Hori, Y., "Electrochemical $CO_2$ Reduction on Metal Electrodes," Modern Aspects of Electrochemisty, No. 42, pp. 89-189, 2008.
Yano, J. et al., "Pulse-Mode Electrochemical Reduction of Carbon Dioxide Using Copper Oxide Electrodes for Selective Ethylene Formation," Journal of Applied Electrochemisty, vol. 38, pp. 1721-1726, Jul. 3, 2008.
Gan, Weijia et al., "Hydrogen Storage and Delivery: Immobilization of a Highly Active Homogeneous Catalyst for the Decomposition of Formic Acid to Hydrogen and Carbon Dioxide," React Kinet Catal Lett., vol. 98, pp. 205-213, Nov. 7, 2009.
Gu, Xiaojun et al., "Synergistic Catalysis of Metal-Organic Framework-Immobilized Au—Pd Nanoparticles in Dehydrogenation of Formic Acid for Chemical Hydrogen Storage," Journal of the American Chemical Society, vol. 133, pp. 11822-11825, 2011.
Boddien, Albert et al., "Efficient Dehydrogenation of Formic Acid Using an Iron Catalyst," Science Magazine, vol. 333, No. 23, pp. 1733-1736, Jul. 8, 2011.
Yi, Nan et al., "Hydrogen Production by Dehydrogenation of Formic Acid on Atomically Dispersed Gold on Ceria," ChemSUSChem Communications, vol. 6, pp. 816-819, 2013.
Jones, John-Paul et al., "Electrochemical $CO_2$ Reduction: Recent Advances and Current Trends," Israel Journal of Chemistry, vol. 54, No. 10, pp. 1451-1466, Sep. 9, 2014.
International Search Report and Written Opinion, Application No. PCT/EP2015/081145, 25 pages, dated Mar. 17, 2016.
Chinese Office Action, Application No. 201580075587.5, 17 pages, dated Jul. 3, 2018.
"Y-Type Zeolites" ACS Material LLC, https://www.acsmaterial.com/blog-detail/y-type-zeolites.html, 3 pages, Aug. 19, 2019.
"Database of Zeolite Structures" MFI: Type Material, https://europe.iza-structure.org/IZA-SC/material_tm.php?STC=MFI, 1 page, Sep. 29, 2020.
"Mordenite" https://www.britannica.com/science/mordenite, 4 pages, Sep. 29, 2020.

* cited by examiner

ELECTROLYSIS SYSTEM FOR CARBON DIOXIDE

CROSS-REFERENCE TO RELATED APPLICATIONS

This application is a U.S. National Stage Application of International Application No. PCT/EP2015/081145 filed Dec. 23, 2015, which designates the United States of America, and claims priority to DE Application No. 10 2015 202 117.3 filed Feb. 6, 2015, the contents of which are hereby incorporated by reference in their entirety.

TECHNICAL FIELD

The present disclosure relates to electrolysis systems and methods. The teachings thereof may be embodied in methods and systems for the utilization of carbon dioxide and production of carbon monoxide.

BACKGROUND

Currently around 80% of worldwide energy demand is generated by the combustion of fossil fuels, the burning of which gives rise to worldwide annual emissions to the atmosphere of approximately 34 000 million tonnes of carbon dioxide. This release into the atmosphere constitute the primary source of carbon dioxide in the atmosphere, which in the case of a lignite power station, for example, can be up to 50,000 tonnes per day. Carbon dioxide is one of the gases known as greenhouse gases, whose negative effects on the atmosphere and the climate are debated. Since carbon dioxide occupies a very low position thermodynamically, it is difficult to reduce it to give reusable products. This fact leaves the recycling of carbon dioxide to date within the realm of theory or of academia.

Natural breakdown of carbon dioxide is accomplished, in one example, by photosynthesis. Photosynthesis is a process broken down temporally and, at a molecular level, spatially into numerous component steps. Therein, carbon dioxide is reacted to form carbohydrates. This process cannot be adapted industrially as it is. Any replica of the natural photosynthesis process using industrial photocatalysis has lacked adequate efficiency.

SUMMARY

Any viable solution should not only enable effective depletion of carbon dioxide but also to ensure economic, long-lived utilization of carbon dioxide. The teachings herein may be embodied in methods and systems for electrochemical carbon dioxide utilization that avoids carbonization.

For example, a method for carbon dioxide utilization by means of an electrolysis system may include: an electrolyte and carbon dioxide ($CO_2$) are passed in front of a cathode (K) through a cathode chamber (KR), the cathode (K) comprises an electrode and/or catalyst material with which carbon dioxide ($CO_2$) is reduced at the cathode (K) and at least one hydrocarbon compound or carbon monoxide (CO) is generated as electrolysis product and also at least one formate is generated as electrolysis byproduct. Electrolysis byproducts are removed from the electrolyte/electrolysis product mixture by means of a catalytic filter system, said catalytic filter system comprising a functionalized complex or a functionalized support material which catalyzes a cleavage reaction of formates to hydrogen ($H_2$) and carbon dioxide ($CO_2$) or to water ($H_2O$) and carbon monoxide (CO).

In some embodiments, the electrolyte is guided in a closed circuit and the filter system is regenerated thermally.

Some embodiments may include an electrolysis system for carbon dioxide utilization, comprising an electrolysis cell (4) having an anode (A) in an anode chamber (AR) and having a cathode (K) in a cathode chamber (KR), and a filter unit (40). The cathode chamber (KR) is designed to take up an electrolysis reactant comprising carbon dioxide ($CO_2$) and to pass it in front of the cathode (K), the cathode (K) comprises an electrode and/or catalyst material by means of which carbon dioxide ($CO_2$) can be reduced to at least one hydrocarbon compound or to carbon monoxide (CO) as electrolysis product and also to at least one formate as electrolysis byproduct. The filter unit (40) comprises at least one catalytic filter system by means of which a formate can be converted to hydrogen ($H_2$) and carbon dioxide ($CO_2$) or to water ($H_2O$) and carbon monoxide (CO).

In some embodiments, the reactable formate is of the type $R^+HCOO^-$ and $R^+$ is a cation from the following group: $H^+$, $Li^+$, $Na^+$, $K^+$, $NH4^+$, $Cs^+$, $Sr^+$, $Ba^+$, $Mn^+$, $Cu^+$.

In some embodiments, the catalytic filter system is based on transition metal complexes, more particularly with a metal from the eighth group of the periodic table or rhodium.

In some embodiments, the catalytic filter system is based on transition-metal-functionalized zeolites, more particularly Y zeolites.

In some embodiments, the catalytic filter system is based on transition-metal-functionalized activated carbon or alumina as support materials.

In some embodiments, the catalytic filter system is based on 3-aminopropyltrimethoxysilane-functionalized zeolites, more particularly Y zeolites.

In some embodiments, the catalytic filter system is immobilized at least partly on the cathode surface.

In some embodiments, the filter unit is implemented as a through-flow filter with incorporated functionalized complexes or support materials as formate scavengers.

In some embodiments, the filter unit (40) comprises a reaction chamber separate from the electrolysis cell (4).

In some embodiments, there is a gas diffusion electrode as formate filter.

Some embodiments include a formate electrolyzer for carbon dioxide utilization and carbon monoxide production based on an electrolysis system as described above, where the cathode comprises lead.

BRIEF DESCRIPTION OF THE DRAWINGS

Embodiments of the present teachings are described with reference to FIGS. 1 to 5 of the appended drawing.

DETAILED DESCRIPTION

Figure 1:
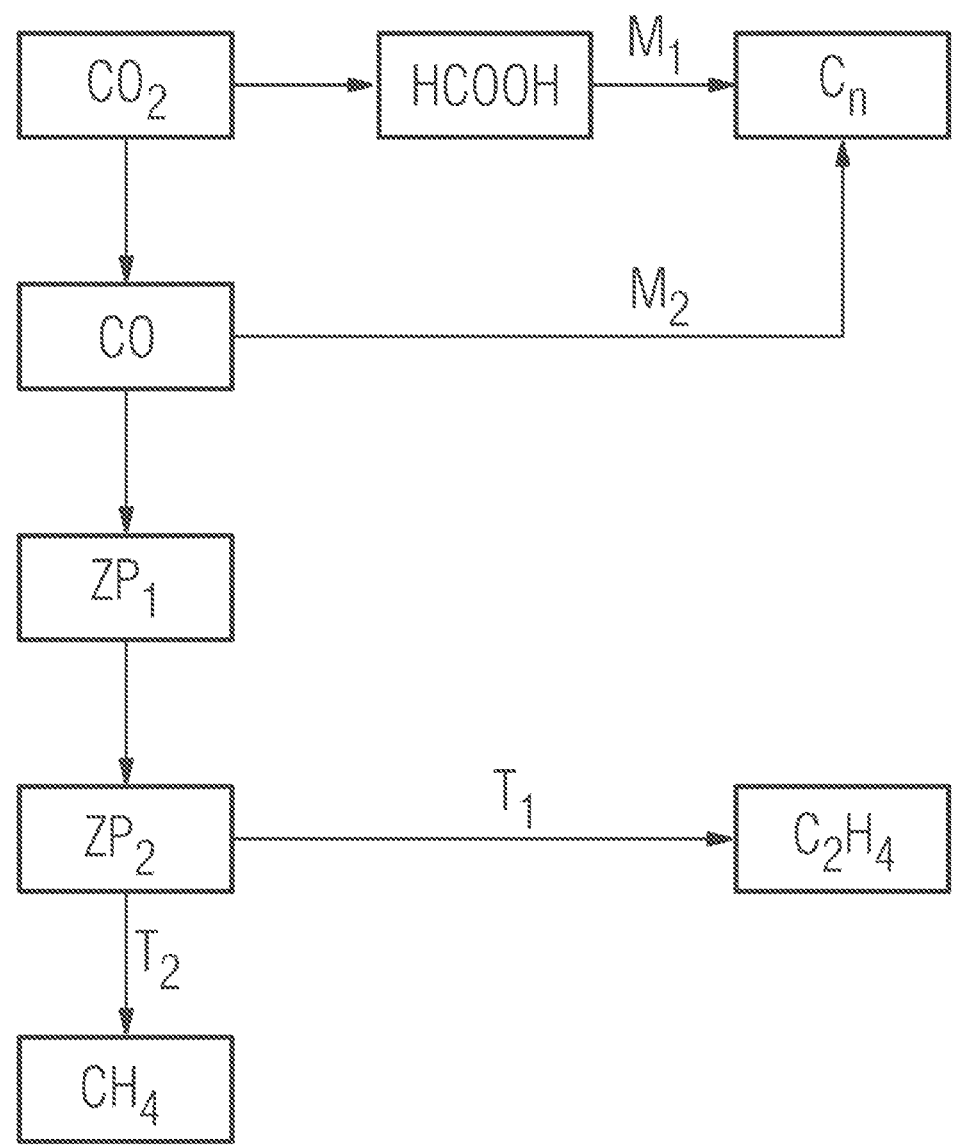
FIG. 1 shows a flow diagram of electrode carbonization, according to teachings of the present disclosure.

One attempt to address the needs described above is the electrochemical reduction of carbon dioxide. Systematic studies of the electrochemical reduction of carbon dioxide are still a relatively young field of development. First efforts to develop an electrochemical system able to reduce an acceptable volume of carbon dioxide emerged only a few years ago. Laboratory-scale research efforts have shown that, preferentially, metals are to be used as catalysts for the electrolysis of carbon dioxide. The publication Electrochemical $CO_2$ reduction on metal electrodes by Y. Hori, published in: C. Vayenas, et al. (Eds.), Modern Aspects of Electrochemistry, Springer, N.Y., 2008, pp. 89-189, reveals Faraday efficiencies over various metal cathodes; see table 1.

While carbon dioxide is reduced almost exclusively to carbon monoxide at silver, gold, zinc, palladium, and gallium cathodes, for example, the reaction products at a copper cathode comprise a multitude of hydrocarbons. At a silver cathode, for example, predominantly carbon monoxide and a little hydrogen are produced. The reactions at anode and cathode may be represented by the following reaction equations:

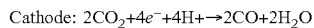

Cathode: $2CO_2 + 4e^- + 4H+ \rightarrow 2CO + 2H_2O$

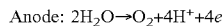

Anode: $2H_2O \rightarrow O_2 + 4H^+ + 4e$

Of particular interest economically, for example, is the electrochemical generation of carbon monoxide, methane, or ethene. These are products which in energetic terms are higher in value than carbon dioxide.

TABLE 1

| Electrode | CH$_4$ | C$_2$H$_4$ | C$_2$H$_5$OH | C$_3$H$_7$OH | CO | HCOO$^-$ | H$_2$ | Total |
|---|---|---|---|---|---|---|---|---|
| Cu | 33.3 | 25.5 | 5.7 | 3.0 | 1.3 | 9.4 | 20.5 | 103.5 |
| Au | 0.0 | 0.0 | 0.0 | 0.0 | 87.1 | 0.7 | 10.2 | 98.0 |
| Ag | 0.0 | 0.0 | 0.0 | 0.0 | 81.5 | 0.8 | 12.4 | 94.5 |
| Zn | 0.0 | 0.0 | 0.0 | 0.0 | 79.4 | 6.1 | 9.9 | 95.4 |
| Pd | 2.9 | 0.0 | 0.0 | 0.0 | 28.3 | 2.8 | 26.2 | 60.2 |
| Ga | 0.0 | 0.0 | 0.0 | 0.0 | 23.2 | 0.0 | 79.0 | 102.0 |
| Pb | 0.0 | 0.0 | 0.0 | 0.0 | 0.0 | 97.4 | 5.0 | 102.4 |
| Hg | 0.0 | 0.0 | 0.0 | 0.0 | 0.0 | 99.5 | 0.0 | 99.5 |
| In | 0.0 | 0.0 | 0.0 | 0.0 | 2.1 | 94.9 | 3.3 | 100.3 |
| Sn | 0.0 | 0.0 | 0.0 | 0.0 | 7.1 | 88.4 | 4.6 | 100.1 |
| Cd | 1.3 | 0.0 | 0.0 | 0.0 | 13.9 | 78.4 | 9.4 | 103.0 |
| Tl | 0.0 | 0.0 | 0.0 | 0.0 | 0.0 | 95.1 | 6.2 | 101.3 |
| Hi | 1.8 | 0.1 | 0.0 | 0.0 | 0.0 | 1.4 | 88.9 | 92.4 |
| Fe | 0.0 | 0.0 | 0.0 | 0.0 | 0.0 | 0.0 | 94.8 | 94.8 |
| Pt | 0.0 | 0.0 | 0.0 | 0.0 | 0.0 | 0.1 | 95.7 | 95.8 |
| Ti | 0.0 | 0.0 | 0.0 | 0.0 | 0.0 | 0.0 | 99.7 | 99.7 |

The table reports Faraday efficiencies [%] of products formed in the reduction of carbon dioxide over various metal electrodes. The figures reported are valued for a 0.1 M potassium hydrogen carbonate solution as electrolyte, and current densities below 10 mA/cm$^2$.

With all electrochemical reduction methods for the conversion of carbon monoxide or carbon dioxide, however, there is a side-effect which occurs and which is frequently unwanted, dependent on the operating conditions: formates, the salts of formic acid, are produced and promote the clogging of free surfaces with carbon deposits. This would deactivate the electrode surface or catalyst surface in an electrolysis cell, since the formation of graphite deposits results in a reduction in the size of the catalytically active surface. In the case of carbon dioxide reduction, there is a diminished conversion, and the selectivity of the catalyst for hydrocarbons is also adversely affected. This implies, equally, detractions from the long-term stability of the electrodes and from the economics of the method.

The problem of catalyst carbonization—that is, the decomposition of the catalyst with graphite—has already been known before from other subject areas relating to the reaction of carbon monoxide or carbon dioxide. In the catalytic cracking process as well, for example, there is catalyst carbonization. In that case the electrodes are not regenerated in situ, but instead must be uninstalled for this purpose. The carbon deposits are then burnt off at temperatures of around 700° C. with the aid of oxygen. An example is the industrially employed FCC (fluid catalytic cracking) process, which is based on the reactor-generator principle.

One approach to countering the problem of catalyst carbonization is known from the subject area of Fischer-Tropsch catalysis, or with methanization reactions. Here, the deactivation of catalyst by deposits of coke is counteracted during the operation. Carbon deposits start to form on unitary metal surfaces, indeed, preferentially when the ratio of the partial pressures of carbon monoxide to hydrogen is greater than 2, at a temperature below 673 K, or greater than 1 in the case of a temperature greater than 673 K. This may be found for example in the publication by M. T. Tavares, I. Alstrup, and C. A. A. Bernardo, published in: Materials and Corrosion 1999, 50, 681-685. Accordingly, the catalyst carbonization during the Sabatier process can be suppressed by an excess of hydrogen. This technique is also situated in too high a temperature range to be able to take place in situ. Therefore these variants cannot be employed in a continuous electrolysis method.

Another variant for regenerating deactivated electrode surfaces is that of reactivation by reversing the polarity of the potential. The polarity of the electrode which functions as cathode is reversed such that the potential at said electrode is in the oxidative range. In that case, of course, the electrode is oxidized itself and, consequently, metal ions may pass into solution. This regeneration method is described for example in the publication by Y. Yano, S. Yamasaki, J. Appl. Electrochem. 2008, 38, 1721-1726. The disadvantages of this technique include the high energy loss as a result of the frequent need for reversal of polarity, and secondly the undesirable downtimes of the system.

Catalytic conversion techniques for the cleaving of formates have also been disclosed before, for example, in chemical hydrogen storage (Boddien, Albert; Mellmann Dorthe; Gartner, Felix; Jackstell, Ralf; Junge, Henrik; Dyson, Paul J.; Laurency, Gabor; Ludwig, Ralf; Beller, Matthias, Science, Volume 333, Issue 6050, pp. 1733-1736 (2011)). Furthermore, the thermal decomposition of transition metal formates has been investigated (Rienacker, W. Toursel, Zeitschrift fur anorganische and allgemeine Chemie, 1961, 307, 235-254). Moreover, the catalytic activity specifically of ruthenium complexes on the reaction of formates is known (C. Fellay, Paul J. D., G. Laurenczy, Angewandte Chemie, 2008, 120, 4030-4032; Weijia Gan, Paul J. Dyson, Gabor Laurenczy, Reaction Kinetics and Catalysis Letters 2009, 98, 205-213). Heterogeneously catalyzed reactions of formates have to date always used a noble metal or a surface modification with a noble metal (Nan Yi, H. Saltsburg, M. F. Stephanopoulos, 2013, 6, 816-819; Xiaojun Gu, Zhang-Hui Lu, Hai-Long Jiang, Tomoki Akita, Qiang Xu, J. Am. Chem. Soc., 2011, 133 (31), 11822-11825; Seung-Young Chung, Sung-Hyun Uhm, Jae-Kwang Lee, Sung-Jin Kang, Yong-Sug Tak, and Jae-Young Lee, J. Ind. Eng. Chem., Vol. 13, No. 3, (2007) 339-344).

The teachings of the present disclosure, in contrast, may allow carbon dioxide utilization by means of an electrolysis system, wherein an electrolyte is passed with carbon dioxide in front of a cathode through a cathode chamber. Carbon dioxide is reduced at the cathode, at least one hydrocarbon compound or carbon monoxide is generated as an electrolysis product, and at least one formate is generated as an electrolysis byproduct. Furthermore, electrolysis byproducts are removed from the electrolyte/electrolysis product mixture by means of a catalytic filter system. The use of the catalytic filter system for the unwanted formates in the electrolysis system, or electrolyte circuit, may allow carbonization of electrode or catalyst as a result of carbon deposits to be prevented and so, in particular, deactivation of a catalyst surface is avoided.

Electrolysis products and electrolysis byproducts are understood to mean substances which are generated by means of electrolysis. Electrolysis products are desired target substances; electrolysis byproducts are substances whose simultaneous cogeneration is essentially unavoidable. Electrolysis byproducts may tend to be substances that are unwanted or frequently unnecessary. Electrolysis reactants are understood to mean substances which are subjected to the electrolysis.

Formates are the salts of formic acid and are in states of dissociation that vary according to pH. In an acidic environment, for example, below the pKa of formic acid, formate is present primarily as formic acid. In a basic environment, formate is present in dissociated form as anions and the corresponding number of cations. The formates which can be reacted in accordance with the invention may typically be represented as follows:

$$R^-HCOO^-$$

where $R^+$ is a cation from the following group:

H+, Li+, Na+, K+, $NH_4$+, Cs+, Sr+, Ba+, Mn+, Cu+.

Another group includes complex cations, of the type occurring, for example, in ionic liquids: wholly or partly alkylated ammonium, phosphonium, sulfonium, piperidinium, morpholinium, pyridinium or imidazolinium or derivatives thereof.

The catalytic filter system may be based on a functionalized complex or support material. The functionalized complexes or support materials used have the capacity to convert formates to hydrogen and carbon dioxide or to water and carbon monoxide, or to promote their reaction. This takes place according to one of the following reaction equations:

$$HCOOH \rightarrow H_2CO_2 \qquad (1a)$$

$$HCOOH \rightarrow H_2O+CO \qquad (1b)$$

The functionalized complexes here are, for example, transition metal complexes, e.g., with a metal from the eighth group of the periodic table or rhodium. Alternatively, the functionalized complexes are transition-metal-functionalized zeolites, more particularly y zeolites, of which Na—Y zeolites are used with particular preference. In another alternative, activated carbon or alumina are used as functionalized support materials. Alumina is the cubic γ-$Al_2O_3$, a starting material for production of ceramics and aluminum. The activated carbon or alumina support materials may be transition-metal-functionalized. Among the functionalized complexes, 3-aminopropyltrimethoxysilane-functionalized zeolites may be used.

In some embodiments, the electrolyte is guided in a closed circuit and the filter system is regenerated thermally. For that purpose, said 3-aminopropyltrimethoxysilane-functionalized Na—Y zeolites are used in a through-flow filter which is incorporated in the electrolyte circuit. In this arrangement they act, so to speak, as formate scavengers. The scavenging mechanism is subject to the reaction shown, in which ammonium formate is formed:

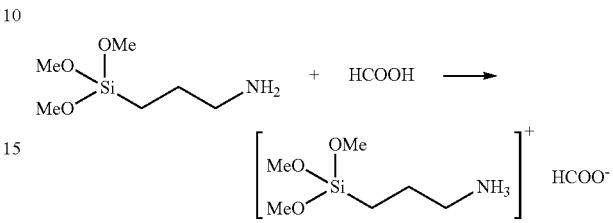

Me here stands for all possible transition metals.

Filter regeneration in this example typically takes place cyclically or batchwise by thermal treatment.

In some embodiments, functionalized complexes or support materials allow the homogeneous and heterogeneous catalytic cleavage of formates in electrolysis systems for carbon dioxide utilization. Functionalized support materials for homogeneous and heterogeneous catalytic cleavage in accordance with the invention may for example be the following:

activated carbon alumina.

Functionalized complexes for homogeneous or heterogeneous catalytic cleavage of formates in electrolysis systems for carbon dioxide utilization may be, for example, the following:

transition metal complexes, more particularly with a metal from the 8th group of the periodic table or rhodium, preferably iron or ruthenium, transition-metal-functionalized zeolites, e.g., Y zeolites, including Na—Y zeolites, 3-aminopropyltrimethoxysilane-functionalized zeolites, e.g., Y zeolites.

The electrolysis system for carbon dioxide utilization may include an electrolysis cell having an anode in an anode chamber and having a cathode in a cathode chamber, and also a filter unit. In some embodiments, the cathode chamber is designed to take up an electrolysis reactant comprising carbon dioxide and pass it in front of the cathode. The filter unit may comprise at least one catalytic filter system by means of which a formate can be converted to hydrogen and carbon dioxide or to water and carbon monoxide. Examples of formates which can be reacted in this way are those of the type $R^+HCOO^-$, where $R^+$ is a cation from the following group: H+, Li+, Na+, K+, $NH_4$+, Cs+, Sr+, Ba+, Mn+, Cu+. Another group are complex cations of the kind which occur, for example, in ionic liquids: wholly or partly alkylated ammonium, phosphonium, sulfonium, piperidinium, morpholinium, pyridinium, or imidazolinium, or derivatives thereof. This electrolysis system with formate filter unit may provide enhanced lifetime by virtue of the resulting avoidance of electrode and/or catalyst carbonization.

In some embodiments, the catalytic filter system comprises transition metal complexes, more particularly with a metal from the 8th group of the periodic table or rhodium. As an alternative to this, the catalytic filter system may also comprise transition-metal-functionalized zeolites, more particularly Y zeolites, with particular preference Na—Y zeolites. In some embodiments, the catalytic filter system comprises transition-metal-functionalized activated carbon or alumina as support materials. Alumina is the cubic γ-$Al_2O_3$, a starting material for production of ceramic and aluminum. In some embodiments, the catalytic filter system comprises 3-aminopropyltrimethoxysilane-functionalized zeolites, more particularly Y zeolites. In this case the scavenging mechanism is subject to reaction (2), shown above, for the formation of ammonium formate, and in this case the filter can be regenerated cyclically or batchwise by thermal treatment.

The catalyst variant with the transition-metal-functionalized complexes or support materials offers the facility of catalytic cleavage of $R^+HCOO^-$ under mild reaction conditions in accordance with one of reactions (1a) and (1b).

"Mild reaction conditions" means that the temperature at which these reactions preferably take place is between 0° C. and 100° C., the reactions being performed more preferably at room temperature. The pressure range of the reactions is between 1 bar and 100 bar, and is preferably 30 bar. The catalytic cleavage to form water and carbon monoxide (1b) in particular has the advantage of allowing very pure carbon monoxide to be obtained. Accordingly, the integration of the formate filter unit into an electrolysis system for carbon dioxide utilization may also be used for carbon monoxide production.

In some embodiments, a catalytic filter system is immobilized at least partly on the cathode surface. This system may have no electroreduction-catalytic activity. This represents a variant of how the filter unit can be integrated into the electrolysis cell. For this purpose, the electrolysis cell preferably comprises a gas diffusion electrode.

In some embodiments, the filter unit comprises a reaction chamber separate from the electrolysis cell. This division may be useful for the thermal regeneration treatment. For example, the separate reaction chamber may be designed as a kind of through-flow filter, in which the functionalized complexes or support materials are incorporated as formate scavengers.

In some embodiments, there is a gas diffusion electrode used as a formate filter. For this purpose, it typically comprises a surface-modified electrode on which the functionalized—for example, heterogenized—complexes or functionalized support materials are immobilized.

The electrolysis systems and methods described permit continuous and effective removal of formates from electrolyte solutions.

Moreover, there is an increase in the efficiency of the systems, not least as a result, for example, of possible recovery of the formic acid from the formates. The systems and methods described do not require electrodes to be uninstalled. The formate filters described can each be used within a closed electrolyte circuit. In some embodiments, the formate filter of a gas diffusion electrode with electrode surface has been modified by heterogenized complex compounds. The corresponding modifications typically have no adverse effect on the electrocatalytic procedure.

In some embodiments, the formate filter or the filter method is utilized to realize a formate electrolyzer for carbon dioxide utilization and carbon monoxide production. Based on an electrolysis system in accordance with the teachings herein, carbon dioxide is reduced to formate at a cathode which comprises a lead fraction in this electrolyzer. At a lead electrode, this operation can be performed with almost 100 percent selectivity. Following the removal of the gases from the electrolyte circuit, the above-described catalytic cleavage of the formates to give water and carbon monoxide is carried out, typically in accordance with reaction equation 1b. Formates generated are in this case no longer considered to be unwanted electrolysis byproducts, but are instead deliberately generated intermediates or reactants for catalysis.

FIG. 1 shows a flow diagram of electrode carbonization. Carbon monoxide CO is only a partial product of the electrochemical reduction of carbon dioxide $CO_2$. Nevertheless, it also still makes a contribution $M_2$, albeit small but nevertheless present, to the overall rate of electrode carbonization. As already mentioned, products from the utilization of carbon dioxide may include carbon monoxide CO, ethene $C_2H_4$, and methane $CH_4$. Ethene $C_2H_4$ and methane $CH_4$ come about via two further intermediate steps, or intermediate $ZP_1$ and $ZP_2$, depending on the mandated reaction temperatures. A first intermediate $ZP_1$ may comprise, for example, Cu—HCO; a second intermediate $ZP_2$ may comprise, for example, Cu—$CH_2$.

At a high temperature $T_2$ of around 321 K, ethene $C_2H_4$ is formed; at a lower temperature $T_1$ of around 273 K, methane is generated. The principal contribution $M_1$ to electrode carbonization comes about via the unwanted byproduct formate $HCOO^-$. The greater the amount of carbon $C_n$ depositing on the electrode and/or the catalyst, the greater the extent to which the active surface area is reduced and therefore the carbon dioxide reduction is diminished.

Figure 2:
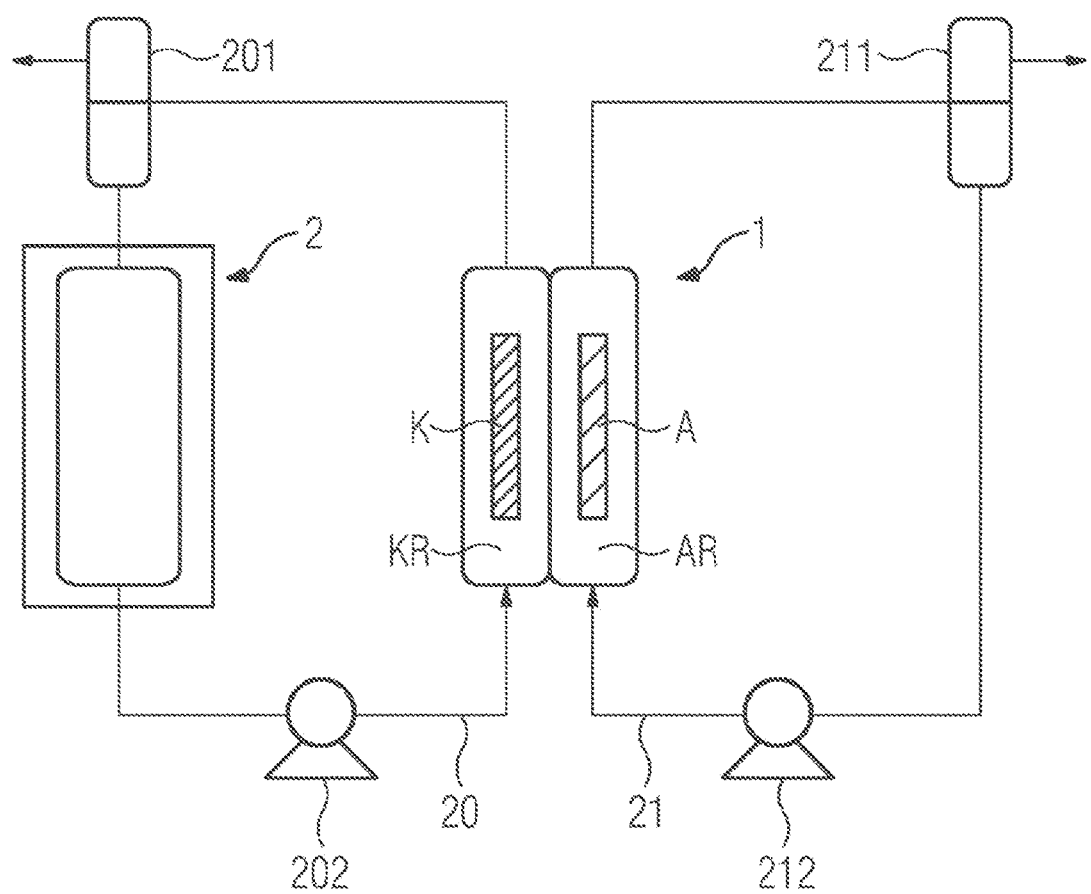
FIG. 2 shows, in diagrammatic representation, an electrolysis system with formate filter, according to teachings of the present disclosure.

FIG. 2 shows diagrammatically an example construction of an electrolysis system. The system may allow the electrolysis and the filter unit to be operated continuously. Two electrolyte circuits are shown, each with a circulation pump. In the anolyte circuit 21, the circulation pump 212 passes the electrolyte through an anode chamber AR in front of an anode A. The through-flow direction is indicated by an arrow. Downstream of the electrolysis cell 1 in the through-flow direction is a phase separator 211, which allows, for example, the oxygen gas $O_2$ formed for example at the anode A to be taken off.

The catholyte circuit 20 likewise has a circulation pump 202, which passes the electrolyte and electrolysis reactants through the cathode chamber KR in front of the cathode K. In the through-flow direction, again indicated by an arrow, there is again a phase separator 201, located downstream of the cathode chamber KR, which allows gases to be taken off from the circuit 20. The gases taken off from the phase separator 201 are, for example, excess carbon dioxide $CO_2$ which has not been reacted. The catholyte circuit 20 further comprises a catalyst unit and/or filter unit 2.

This division may be employed for thermal regeneration treatment. For example, the separate reaction chamber 2 may function as a through-flow filter, in which the functionalized complexes or support materials are incorporated as formate scavengers. The integrated filter unit 2 in the catholyte circuit 20 prevents formates from accumulating increasingly in the cathode circuit and therefore blocking the catalytic centers by deposition of graphite.

Figure 3:
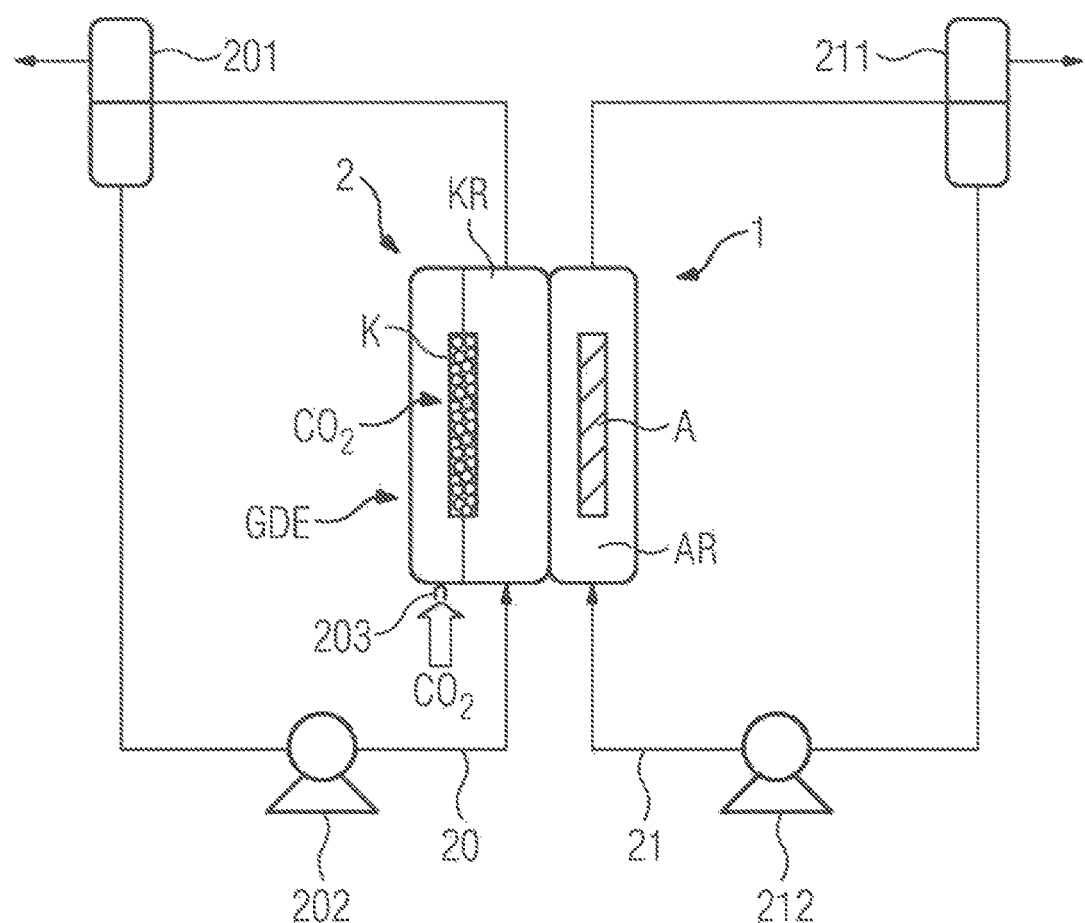
FIG. 3 shows, in diagrammatic representation, an electrolysis system with gas diffusion electrode, according to teachings of the present disclosure.

Alternatively, the catalyst unit and/or filter unit 2 could be integrated in the cathode chamber KR. This could be realized, for example, in the form of a gas diffusion electrode GDE. The electrolysis system shown in FIG. 3 differs from that in FIG. 2 in the construction of the electrolysis cell 1: instead of a two-compartment construction, the cell now has a gas diffusion electrode GDE. For introduction of the carbon dioxide $CO_2$ into the catholyte circuit 20, the gas diffusion electrode GDE comprises a carbon dioxide inlet 203; the cathode K is gas-permeable to carbon dioxide $CO_2$. A gas diffusion electrode GDE is characterized in that a liquid component, such as an electrolyte, and a gaseous component, such as an electrolysis reactant, can be brought into contact with one another in a pore system of the electrode, such as the cathode K, for example. The pore system of the electrode is in this case implemented in such a way that the liquid phase and the gaseous phase are able equally to penetrate the pore system and may be present simultaneously therein.

For this purpose, typically, a reaction catalyst is porous in design and takes on the electrode function, or a porous electrode has catalytically active components. In the present example, the gas diffusion electrode GDE may comprise the formate scavengers, in other words the functionalized—for example, heterogenized—complexes or functionalized support materials. These complexes or materials may be immobilized on a surface-modified electrode or on other internal surfaces of the cathode chamber KR.

Figure 4:
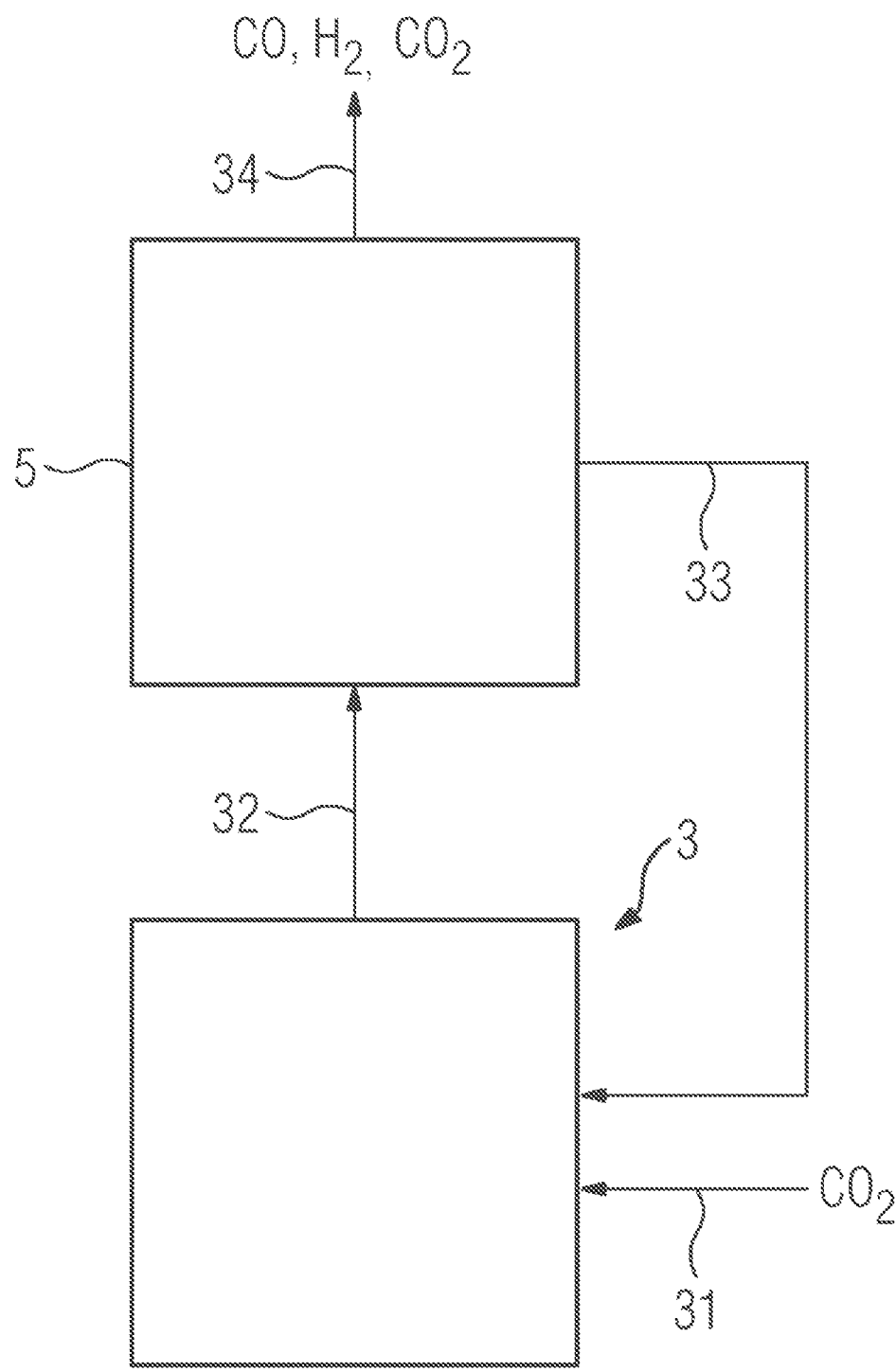
FIG. 4 shows, diagrammatically, a catholyte circuit of a carbon monoxide electrolyzer, according to teachings of the present disclosure.
Figure 5:
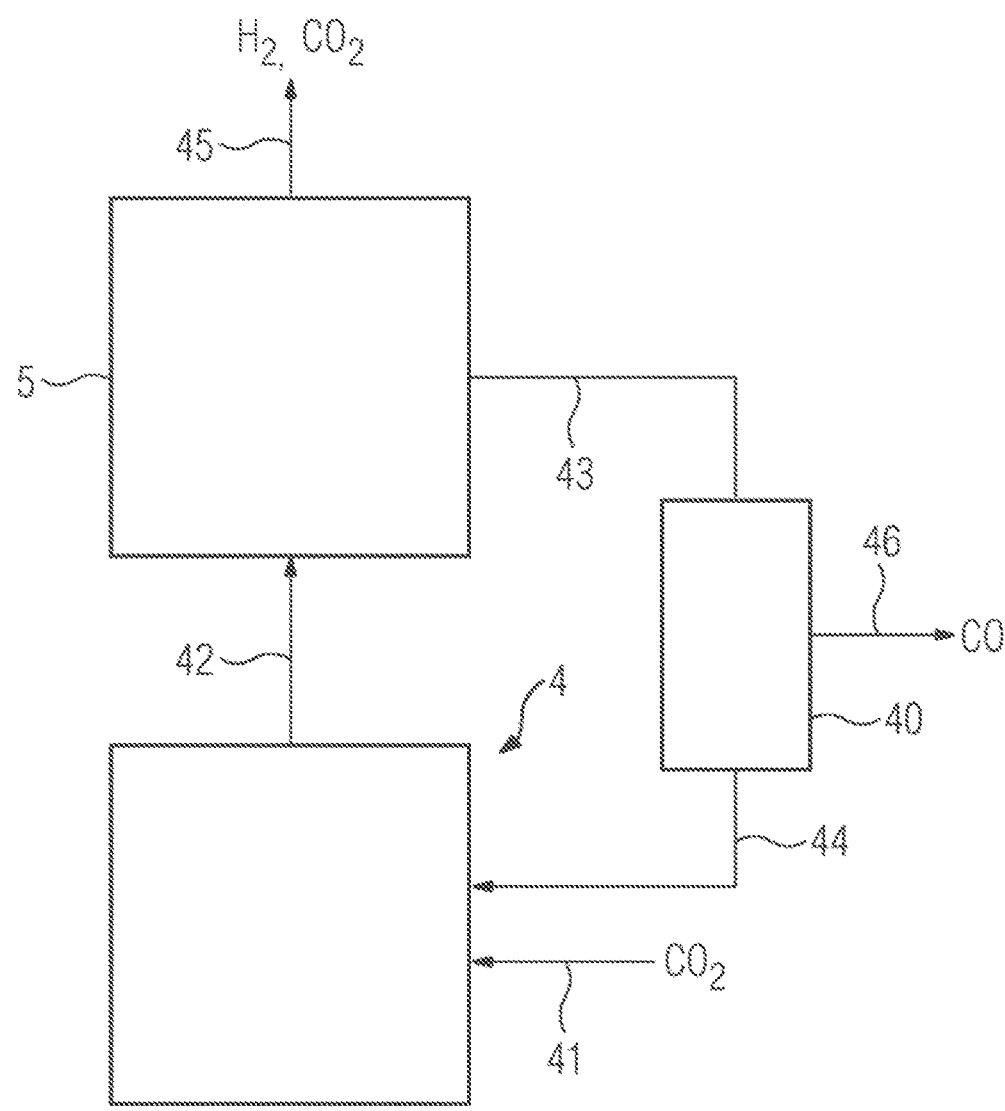
FIG. 5 shows, diagrammatically, a catholyte circuit of a formate electrolyzer, according to teachings of the present disclosure.

FIGS. 4 and 5 depict by way of example the catholyte circuits of a carbon monoxide electrolyzer and of a formate electrolyzer. FIG. 4 illustrates the problem of recovering pure products from a carbon dioxide utilization procedure by means of electrolysis: as a result of the selectivity of the electrodes used, the reduction products can be predetermined up to a certain percentage fraction. The recovery of pure carbon monoxide CO from a carbon dioxide reduction is not possible, however. As shown in FIG. 4, there are always a plurality of products leaving the electrolysis cell 3: carbon monoxide CO, carbon dioxide $CO_2$, and hydrogen $H_2$.

Following gas removal 5, these products can be taken off from the system in the form of a gas mixture 34, while the electrolyte is introduced back into the electrolysis cell 3 via—for example—the line 33 in a circuit.

Also shown in FIG. 4 is the carbon dioxide feed 31. For example, the carbon dioxide $CO_2$, when a gas diffusion electrode is used, may be introduced into the system at this point or introduced into the electrolyte circuit via a separate carbon dioxide reservoir. In complete contrast to the hydrogen electrolyzers, the separation between products in the case of the carbon dioxide electrolysis, in other words between the carbon monoxide CO and the reactants, the carbon dioxide $CO_2$, indeed, is evidently much more complicated, since both products and reactants are in gas form.

Making use of the catalytic decomposition reaction of HCOOH or HCOO to form $H_2O$ and CO (1c), very pure carbon monoxide CO can also be recovered from the catalyst and filter unit 2, in addition to its filter effect. In the formate electrolyzer of the invention, the formates $R^+HCOO^-$ that can be generated with virtually 100% selectivity from carbon dioxide $CO_2$ are exploited accordingly. In this method and in this device for carbon dioxide utilization, these formates are no longer unwanted reaction byproducts, but are instead deliberately generated intermediates on the path to carbon monoxide production. In the formate electrolyzer shown in FIG. 5, therefore, it is not carbon dioxide $CO_2$ which is reduced to carbon monoxide CO in the electrolysis cell 4; instead, the carbon dioxide $CO_2$ is reduced to formate $R^-HCOO^-$ at a lead electrode. This formate is in solution in the electrolyte, and this intermediate can then be separated off from the unreacted gaseous reactant, in other words the carbon dioxide $CO_2$, by a gas removal procedure. This also means, for example, that in this case there is no need for an expensive silver electrode to be used.

The formate-containing electrolyte is then passed on via the catalyst and/or filter unit 40. The formate cleavage reaction takes place in this filter unit 40: the formate $R^+HCOO^-$ is converted into carbon monoxide CO, preferably in accordance with reaction 1b. In contrast to the standard electrolysis of carbon dioxide $CO_2$, in which carbon monoxide CO can be generated together with hydrogen $H_2$ and carbon dioxide $CO_2$ impurities, which may run to a fraction of up to several percent, it is possible using the formate electrolyzer to produce very pure carbon monoxide CO. The impurities in that case are now only in the parts-per-thousand range. A further particular advantage is that the formate electrolyzer does not require any additional, complicated gas removal. Hence it is possible to produce hydrogen-free carbon monoxide CO, which is currently a very expensive resource in the chemical industry, and at the same time it is possible to provide an effective, long-lived electrolysis system for the utilization of carbon dioxide.

What is claimed is:

1. An electrolysis system for carbon dioxide utilization, the system comprising:
   an electrolysis cell having an anode in an anode chamber, a cathode in a cathode chamber, and a filter unit;
   wherein the cathode chamber takes up an electrolysis reactant comprising carbon dioxide and passes it in front of the cathode;
   wherein the cathode comprises an electrode or catalyst material to reduce carbon dioxide to at least one of a hydrocarbon compound, carbon monoxide, or a formate; and
   wherein the filter unit comprises a catalytic filter system with a catalyst material at least partially immobilized on a surface of the cathode;
   wherein the catalyst material of the catalytic filter system is not electroreductively catalytically active; and
   wherein the catalytic filter system includes a functionalized complex or a functionalized support material which catalyzes a cleavage reaction to convert any formate present to: (a) hydrogen and carbon dioxide, or (b) water and carbon monoxide.

2. The electrolysis system as claimed in claim 1, wherein the reactable formate is of the type R+HCOO–where R+ is a cation selected from the group consisting of: H+, Li+, Na+, K+, NH4+, Cs+, Sr+, Ba+, Mn+, and Cu+.

3. The electrolysis system as claimed in claim 1, wherein the catalytic filter system comprises transition metal complexes, including a metal from the eighth group of the periodic table or rhodium.

4. The electrolysis system as claimed in claim 1, wherein the catalytic filter system comprises transition-metal-functionalized activated carbon or alumina as support materials.

5. The electrolysis system as claimed in claim 1, wherein the catalytic filter system comprises 3-aminopropyltrimethoxysilane-functionalized zeolites.

6. The electrolysis system as claimed in claim 1, comprising a gas diffusion electrode functioning as a formate filter.

7. The electrolysis system as claimed in claim 1, wherein the cathode comprises lead.

* * * * *